(12) United States Patent
Choi et al.

(10) Patent No.: US 7,234,217 B2
(45) Date of Patent: *Jun. 26, 2007

(54) DEVICE FOR COUPLING PCB SHEET HAVING POSITION DECIDING JIG PART

(75) Inventors: Bong Kyu Choi, Chungcheongnam-do (KR); Chun Ho Choi, Kyungki-do (KR)

(73) Assignee: Samsung Electro-Mechanics Co., Ltd., Kyungki-Do (KR)

( * ) Notice: Subject to any disclaimer, the term of this patent is extended or adjusted under 35 U.S.C. 154(b) by 64 days.

This patent is subject to a terminal disclaimer.

(21) Appl. No.: 11/038,050

(22) Filed: Jan. 21, 2005

(65) Prior Publication Data

US 2005/0128725 A1 Jun. 16, 2005

Related U.S. Application Data

(60) Continuation of application No. 10/177,664, filed on Jun. 24, 2002, now Pat. No. 7,017,248, which is a division of application No. 09/510,298, filed on Feb. 22, 2000, now Pat. No. 6,574,862.

(30) Foreign Application Priority Data

| Feb. 23, 1999 | (KR) | ............................... 1999-05914 |
| Oct. 11, 1999 | (KR) | ............................... 1999-43714 |
| Oct. 11, 1999 | (KR) | ............................... 1999-43715 |
| Oct. 11, 1999 | (KR) | ............................... 1999-43716 |
| Oct. 11, 1999 | (KR) | ............................... 1999-43717 |

(51) Int. Cl.
*B23P 19/04* (2006.01)

(52) U.S. Cl. ............... 29/402.08; 29/739; 29/740; 29/830; 29/832; 174/250; 174/255; 361/732; 361/740; 361/801; 361/802

(58) Field of Classification Search ............. 29/830, 29/831, 402.08, 832; 174/250, 255, 52.1; 361/801, 802, 732, 740

See application file for complete search history.

(56) References Cited

U.S. PATENT DOCUMENTS 3,638,573 A * 2/1972 Campbell .................. 102/364

(Continued)

FOREIGN PATENT DOCUMENTS

JP 5-063351 3/1993

(Continued)

*Primary Examiner*—Rick Kiltae Chang
(74) *Attorney, Agent, or Firm*—Lowe Hauptman & Berner

(57) ABSTRACT

A method and a device for coupling a PCB sheet are disclosed. If a defective PCB is found after the manufacture of continuously arranged circuit patterns, then the defective PCB sheet portion is removed to replace it with a new PCB sheet portion. That is, a defective circuit pattern sheet 2' is removed from continuously arranged circuit patterns of a first PCB sheet 4a. After removal of the defective circuit pattern sheet 2', the first PCB sheet 4a is position-located by means of a position locating means 12. Then the space which is formed by removing the defective circuit pattern sheet 2' is filled with a second PCB sheet 4b on which a good quality circuit pattern 2b is printed. Then the first PCB sheet 4a and the second PCB sheet 4b are coupled together by using an adhesive means 14.

18 Claims, 18 Drawing Sheets

U.S. PATENT DOCUMENTS

| | | | |
|---|---|---|---|
| 4,445,952 A | 5/1984 | Reynolds et al. | |
| 4,588,468 A | 5/1986 | McGinty et al. | |
| 4,588,626 A | 5/1986 | Cologna et al. | |
| 4,743,468 A | 5/1988 | Jimenez | |
| 5,401,152 A | 3/1995 | Jacino et al. | |
| 5,426,568 A * | 6/1995 | Lamers et al. | 361/810 |
| 5,528,826 A * | 6/1996 | Boudreau | 29/830 |
| 5,925,204 A | 7/1999 | Hoffmann | |
| 5,955,113 A | 9/1999 | Jacino et al. | |
| 6,039,824 A | 3/2000 | Van Haandel | |
| 6,106,648 A | 8/2000 | Butt | |
| 6,171,116 B1 | 1/2001 | Wicks et al. | |
| 6,342,682 B1 * | 1/2002 | Mori et al. | 174/262 |
| 6,574,862 B1 | 6/2003 | Choi et al. | |
| 6,782,613 B1 * | 8/2004 | Wark et al. | 29/842 |
| 7,017,248 B2 | 3/2006 | Choi et al. | |

FOREIGN PATENT DOCUMENTS

| | | |
|---|---|---|
| JP | 5-277994 | 10/1993 |
| JP | 6-310820 | 11/1994 |
| JP | 8-222819 | 8/1996 |
| JP | 9-130001 | 5/1997 |
| JP | 10-247656 | 9/1998 |
| JP | 11-040903 | 2/1999 |

* cited by examiner

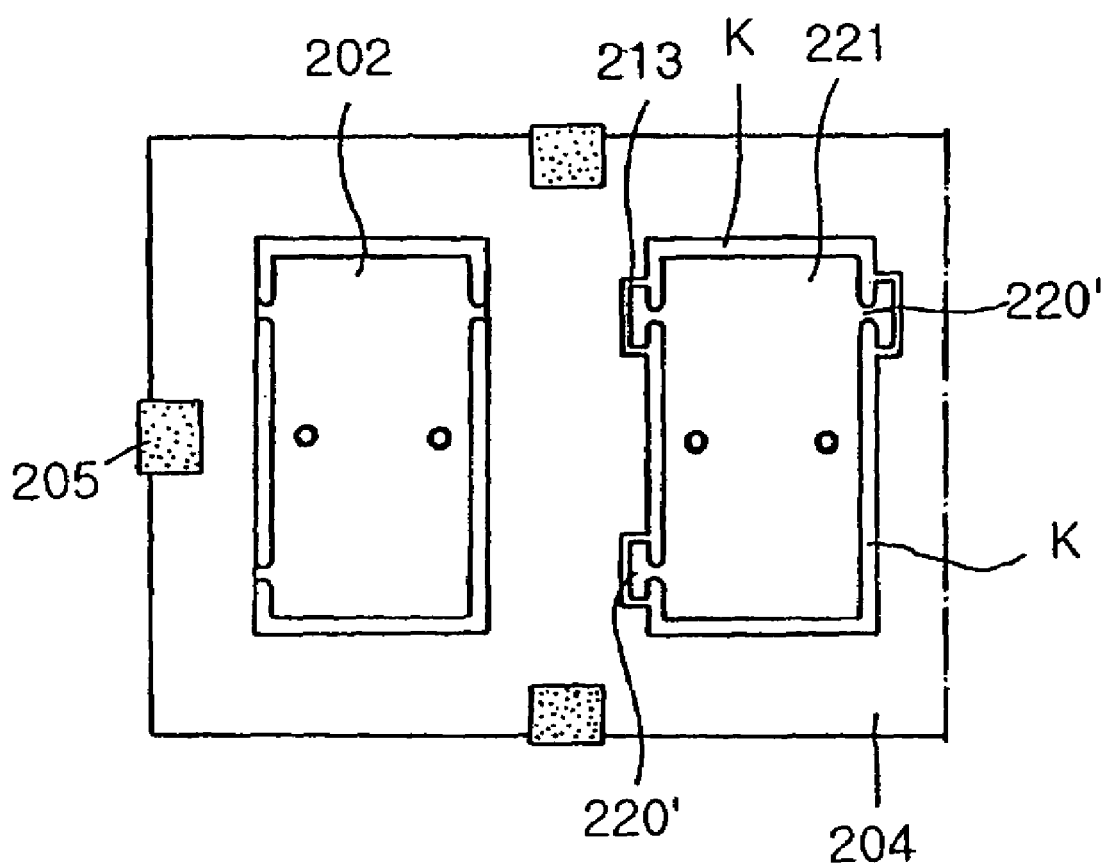
FIGG. 12A

DEVICE FOR COUPLING PCB SHEET HAVING POSITION DECIDING JIG PART

RELATED APPLICATIONS

The present application is a continuation of and claims priority from application Ser. No. 10/177,664, filed Jun. 24, 2002, now U.S. Pat. No. 7,017,248, issued Mar. 28, 2006, which is a divisional of application Ser. No. 09/510,298, filed Feb. 22, 2000, now U.S. Pat. 6,574,862 issued Jun. 10, 2003, the disclosure of which is hereby incorporated by reference herein in its entirety.

BACKGROUND OF THE INVENTION

1. Field of the Invention

The present invention relates to a method and a device for coupling a printed circuit board (to be called PCB below) sheet, in which a plurality of PCBs are continuously arranged on a sheet when manufacturing the PCBs, and if a defective PCB is found after the manufacture, then the defective PCB sheet portion is removed to replace it with a new PCB sheet portion. Particularly, the present invention relates to a method and a device for coupling a PCB sheet, in which in a continuously printed PCBs on a sheet, a defective portion is removed, a first PCB sheet formed by the removal is located by a position locating means to be filled with a second PCB sheet of a good quality circuit pattern, and an adhesive material is spread on a space area between the first PCB sheet and a second PCB sheet, thereby making the arrangement of the PCBs continuous. Thus the defective PCB is removed, and a good quality PCB is replaced into the place in an easy manner, so that the defective PCB can be turned to a good quality portion.

2. Description of the Prior Art

Generally, as shown in FIG. 1, in the conventional PCB sheet structure, a plurality of circuit patterns 51, 51' and 51" are arranged and continuously printed upon a PCB sheet 52.

In this conventional PCB sheet 52, the plurality of the circuit patterns 51, 51' and 51" are printed, and then, the quality of the total of the circuit patterns is checked by using a jig and a fixture. Then the acceptable PCB sheets 52 are used as the final product. However, if anyone of the plurality of the circuit patterns is defective, then the whole PCB sheet on which the plurality of the circuit patterns 51, 51' and 51" are printed has to be discarded.

That is, if any one of the plurality of the circuit patterns is found, to be defective upon inspecting them, even the good circuit patterns have to be discarded.

As a result, the material loss is high because of the discarding of the total sheet, and the workability and productivity are aggravated, as well as increasing the production cost.

SUMMARY OF THE INVENTION

The present invention is intended to overcome the above described disadvantages of the conventional technique.

Therefore it is an object of the present invention to provide a device for coupling a PCB sheet, in which defective circuit pattern portions are removed from a continuously arranged circuit pattern sheet to replace with new ones, so that a whole circuit pattern sheet can be saved without being discarded, thereby increasing the product yield, and curtailing the production cost.

It is another object of the present invention to provide a method for coupling a PCB sheet, in which defective circuit pattern portions are cut away from a continuously arranged circuit pattern sheet, and the cut space is filled with new ones by using a position locating means, the filling being carried out in a simple manner by using a heat resistant tape and an adhesive means containing a hardening agent, thereby improving the workability and the productivity.

In achieving the above objects, the device for coupling a PCB sheet according to the present invention includes: a position locating means disposed upon a PCB securing plate, for locating the position of a second PCB sheet of a good quality circuit pattern to fill a space after removing a PCB sheet of a defective circuit pattern from a continuously arranged circuit patterns of a first PCB sheet; a PCB securing means attached on the PCB securing plate, for preventing loose movements of the first and second PCB sheets; a space for putting an adhesive means into between the first and second PCB sheets (which are secured on the PCB securing plate); and the adhesive means being filled into the space between the first and second PCB sheets to be cured so as to couple the first and second PCB sheets together.

In another aspect of the present invention, the method for coupling a PCB sheet according to the present invention includes the steps of: cutting a defective PCB sheet of a defective circuit pattern to remove it from a continuously arranged circuit patterns of a first PCB sheet (defective circuit pattern removing step); filling a vacant place of the removed defective PCB sheet with a second PCB sheet of a good quality circuit pattern by utilizing a position locating means (PCB sheet position locating step); placing the first and second PCB sheets on a PCB securing plate by using a PCB securing means to prevent any loose movements of them, and filling an adhesive (with a volatile component being removed) into a space between the first and second PCB sheets to cure the adhesive at a temperature of 120–200° C. within a drying furnace (adhesive injecting and curing step); and removing the position locating means to separate the PCB securing plate from the PCB sheet after a curing of the adhesive (PCB securing plate separating step).

BRIEF DESCRIPTION OF THE DRAWINGS

The above objects and other advantages of the present invention will become more apparent by describing in detail the preferred embodiment of the present invention with reference to the attached drawings in which:

FIGS. 12A and 12B are plan views showing the coupling of a new good quality PCB sheet to the whole PCB sheet in the third embodiment of the present invention;

DETAILED DESCRIPTION OF THE PREFERRED EMBODIMENTS

The preferred embodiments of the present invention will be described referring to the attached drawings.

Figure 1:
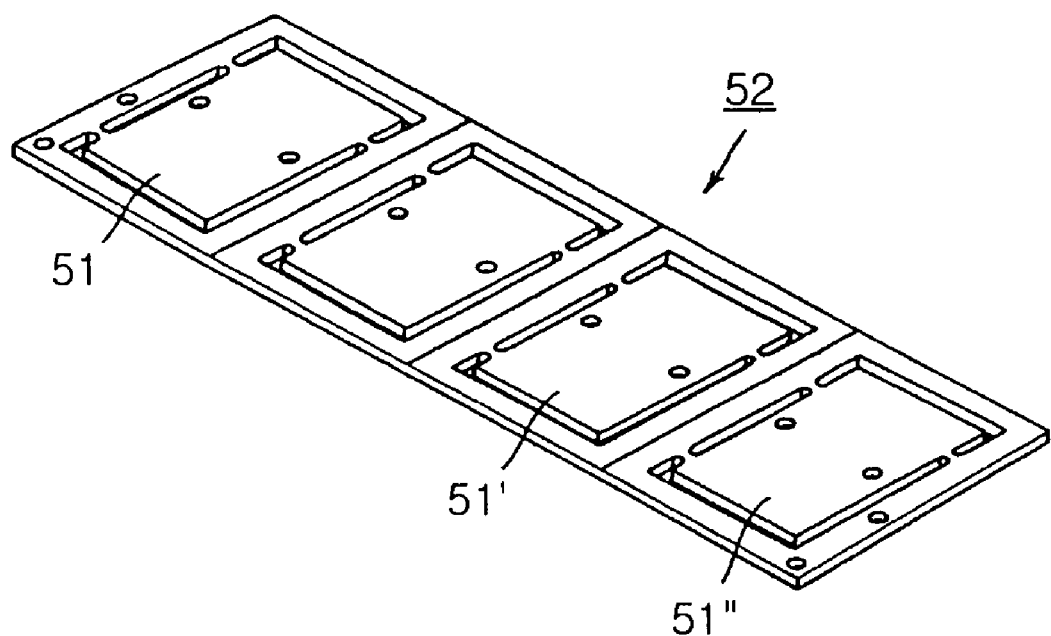
FIG. 1 is a perspective view of the general PCB sheet in which circuit patterns are continuously printed on a sheet.
Figure 2:
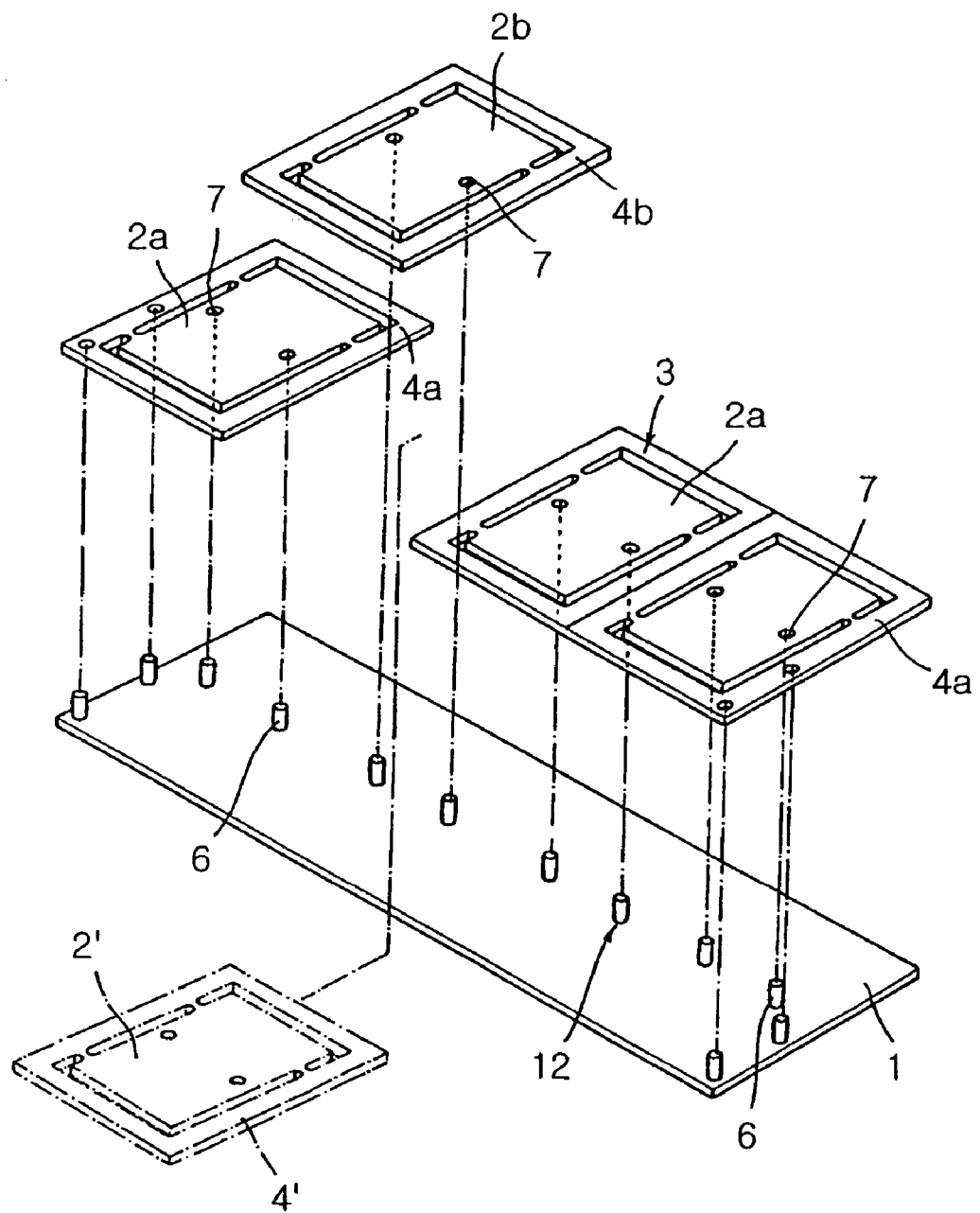
FIG. 2 is an exploded perspective view showing the coupling of the first and second PCB sheets, the sheets being fixed on the PCB securing plate according to the present invention.
Figure 3:
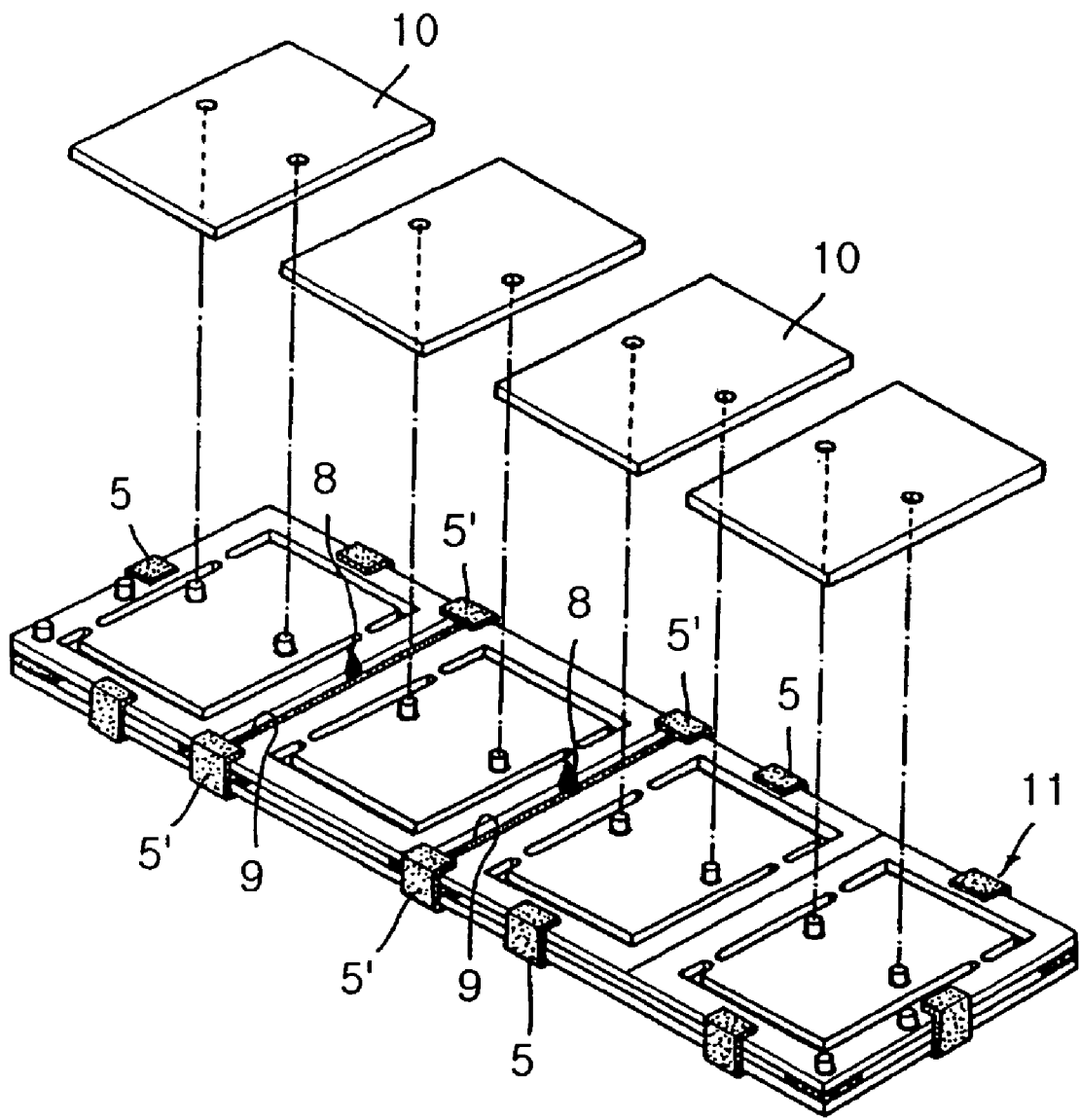
FIG. 3 is a schematic view showing the coupled state of the first and second PCB sheets according to the present invention.
Figure 4:
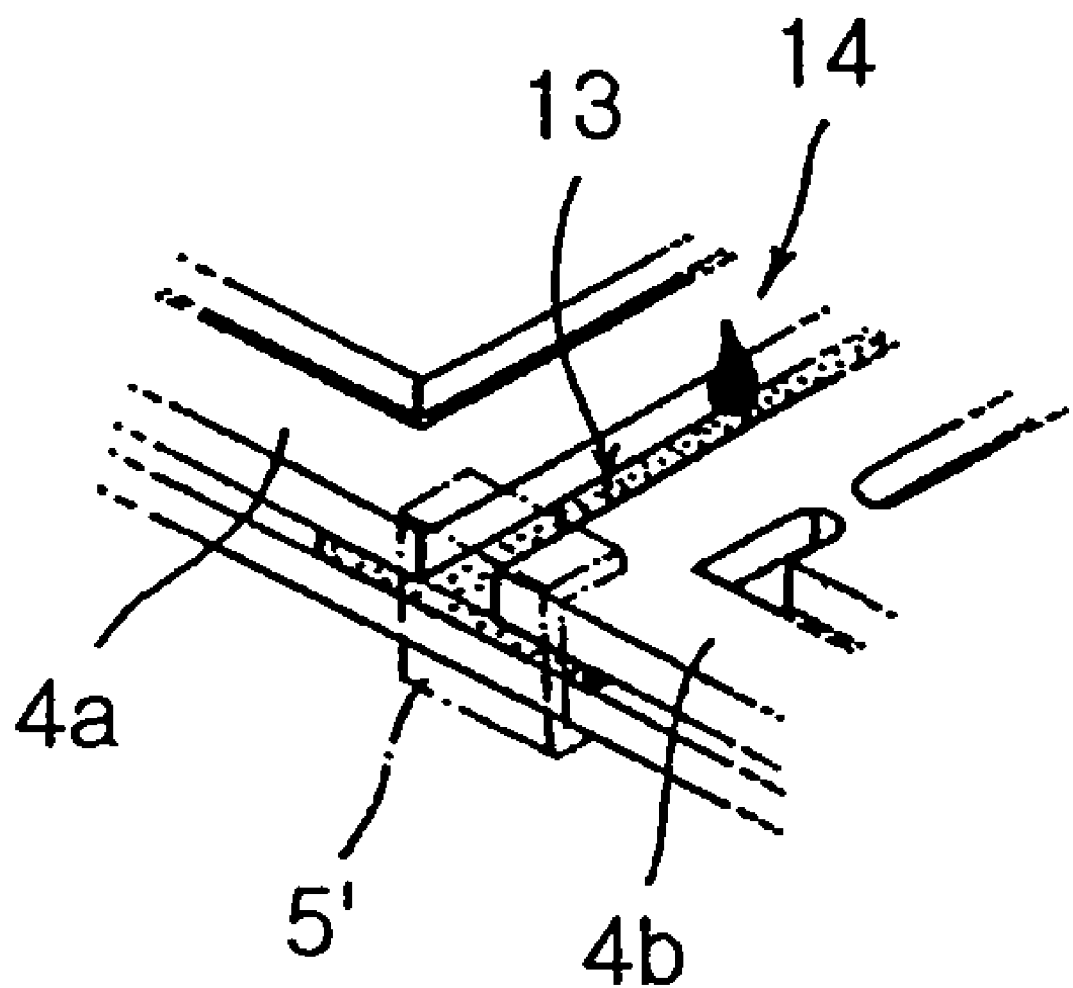
FIG. 4 illustrates in detail the coupling portion of the first and second PCB sheets according to the present invention.
Figure 5:
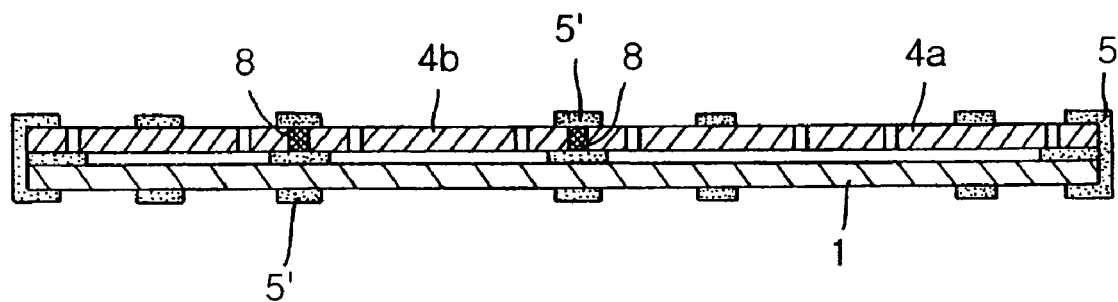
FIG. 5 is a frontal sectional view showing the coupled state of the first and second PCB sheets according to the present invention.

FIG. 2 is an exploded perspective view showing the coupling of the first and second PCB sheets, the sheets being fixed on the PCB securing plate according to the present invention. FIG. 3 is a schematic view showing the coupled state of the first and second PCB sheets according to the present invention.

A first PCB sheet 4a on which a plurality of circuit pattern parts 2 are printed is disposed on a PCB securing plate 1. A second PCB sheet 4b on which a good quality circuit pattern part 2 is printed is put to a place where a defective circuit pattern part 2' of a first PCB sheet 4a has been removed. The second PCB sheet 4b is placed by being located by a PCB securing means 11.

The first and second PCB sheets 4a and 4b are fixed to the PCB securing plate 1 by means of PCB securing tapes 5 which are the constituents of the PCB securing means 11. Thus any loose movements of the first and second PCB sheets 4a and 4b are prevented.

A plurality of PCB securing pins 6 upstand on the PCB securing plate 1, while the first and second PCB sheets 4a and 4b are provided with a plurality of pin receiving holes 7 correspondingly with the PCB securing pins 6. Thus the PCB securing pins 6 of the PCB securing plate 1 are inserted into the pin receiving holes 7 to support the PCB sheets 4a and 4b.

A space 13 is formed between the first and second PCB sheets 4a and 4b, so that an adhesive 8 of an adhesive means 14 can be injected into a channel 9 of the space 13. A tape 5' is put to the bottom, front and rear of the channel 9 of the space 13, so that the adhesive can be prevented from being leaked.

A cover 10 covers the first and second PCB sheets 4a and 4b to protect the circuit patterns of the first and second PCB sheets 4a and 4b. The adhesive 8 which has been injected into the channel 9 is cured to couple the first and second PCB sheets 4a and 4b together.

Now the method for the PCB sheet according to the present invention will be described.

As shown in FIGS. 2 to 5, if any one of the circuit pattern parts 2 which constitute a PCB sheet 3 is found to be defective upon testing by a tester (not illustrated), then the defective sheet part 4' of the defective circuit pattern part 2' is cut off by using a router or another cutter. Then a second PCB sheet 4b on which a good quality circuit pattern part 2 is printed is prepared and is disposed to the cut space to be coupled with the first PCB sheet 4a.

Then the first PCB sheet 4a which is coupled with the second PCB sheet 4b is secured to the PCB securing plate 1. Under this condition, the plurality of the PCB securing pins 6 are inserted into the plurality of the pin receiving holes 7, with the result that the first and second PCB sheets 4a and 4b are supported on the PCB securing plate 1, with the sheets 4a and 4b being separated by a certain distance.

Then the first and second PCB sheets 4a and 4b are fixed to the PCB securing plate 1 by using a PCB securing tape 5 which is a both-face tape, so that any loose movements of the first and second PCB sheets 4a and 4b can be prevented. Under this condition, it is made sure that the PCB securing tape 5 should be only minimally affected by the thermal deformation. That is, a heat resistant tape is used, so that the tape can be easily removed upon completion of the coupling of the first and second PCB sheets 4a and 4b.

Meanwhile, between the first and second PCB sheets 4a and 4b which are disposed on the PCB securing plate 1, there is provided a separation distance L of about 1–5 mm. Thus there is formed a space 13 which forms a channel 9. Then a heat resistant tape 5' is put to the bottom, front and rear of the channel 9, so that the injected adhesive can be prevented from being leaked.

If the separation distance L between the first and second PCB sheets 4a and 4b is less than 1 mm, then the first and second PCB sheets 4a and 4b cannot be sufficiently strongly coupled together. On the other hand, if the separation distance L is more than 5 mm, although the first and second PCB sheets 4a and 4b can be sufficiently strongly coupled together, the expensive adhesive is too much consumed, and therefore, the economy is aggravated. Preferably, the separation distance should be about 2 mm, and the volume of the injected adhesive 8 should be slightly smaller than or equal to the volume of the channel 9.

Thus the first and second PCB sheets 4a and 4b are secured by using the PCB securing tape 5 and the tape 5', the latter surrounding the channel 9 of the space 13. Then the adhesive 8 is injected into the channel 9 of the space 13 which is formed between the first and second PCB sheets 4a and 4b. Then the whole structure is transferred to a drying furnace to make the adhesive 8 cured at a temperature of 120–200° C. Under this condition, the volatile component of the adhesive 8 has been removed in advance, and therefore, the thermal deformations such as the thermal expansion and the thermal contraction are made to be minimal. Further, a hardening agent such as a highly heat resistant epoxy resin is added to the adhesive, and the proportion of the hardening agent is 1–5 wt % as against 99–95 wt % of the adhesive.

After the injection of the adhesive 8, the circuit patterns of the first and second PCB sheets 4a and 4b are covered with a flat cover part 10 to protect the first and second PCB sheets 4a and 4b from the heat. The adhesive 8 which has been injected into the channel 9 is exposed to the outside so as to be cured. Then the whole structure which consists of the first and second PCB sheets 4a and 4b and the PCB securing plate 1 is transferred to a drying furnace to make the adhesive 8 cured at a temperature of 120–200° C.

After the completion of the curing of the adhesive 8, the tape 5' is removed from around the channel 9, and the PCB securing plate 1 is separated from the first and second PCB sheets 4a and 4b, thereby completing the coupling of the first and second PCB sheets 4a and 4b together.

Figure 6:
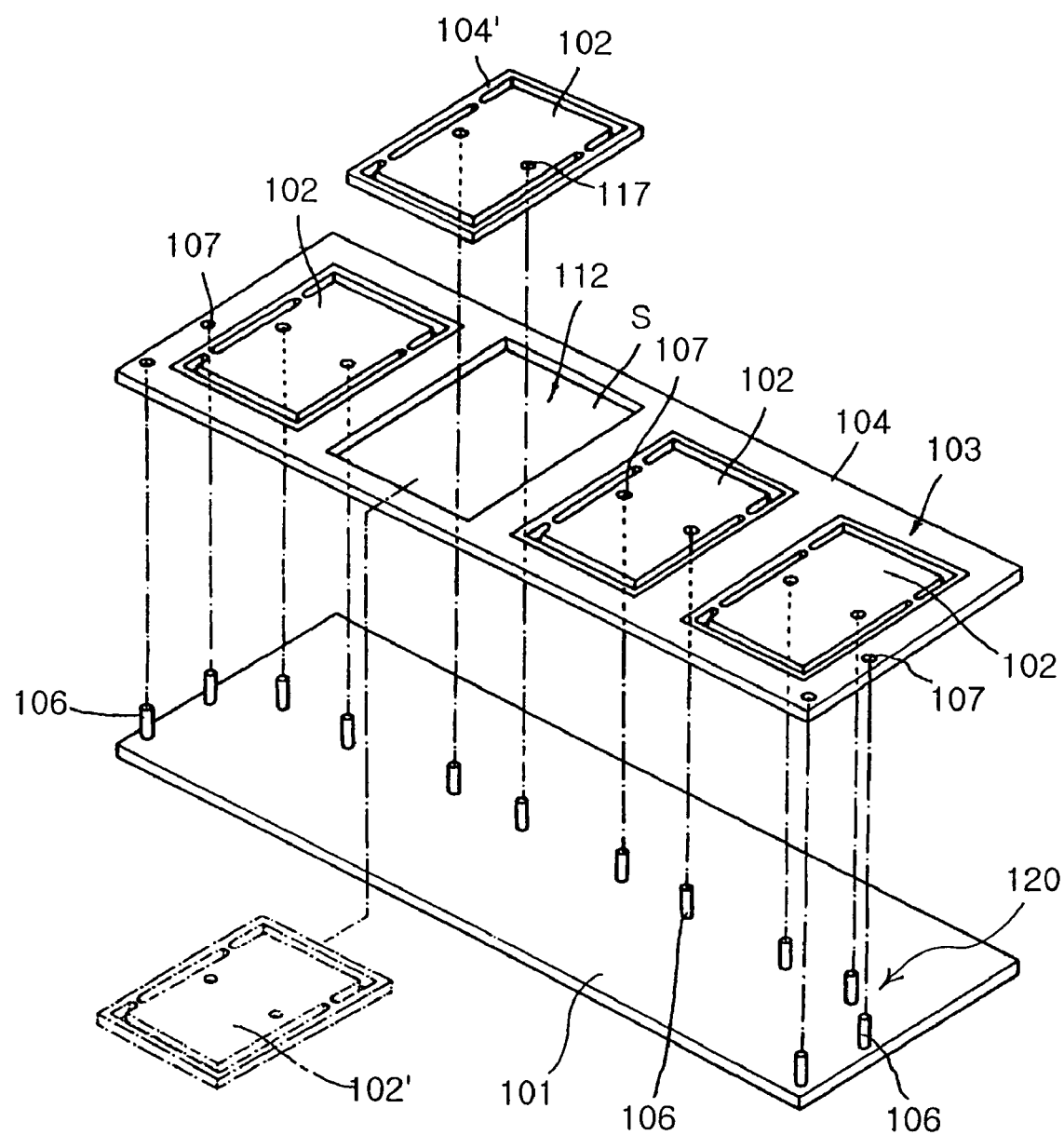
FIG. 6 illustrates a state in which the second PCB sheet is inserted into the first PCB sheet, and the two sheets are fixed onto the PCB securing plate, in a second embodiment of the present invention.
Figure 7:
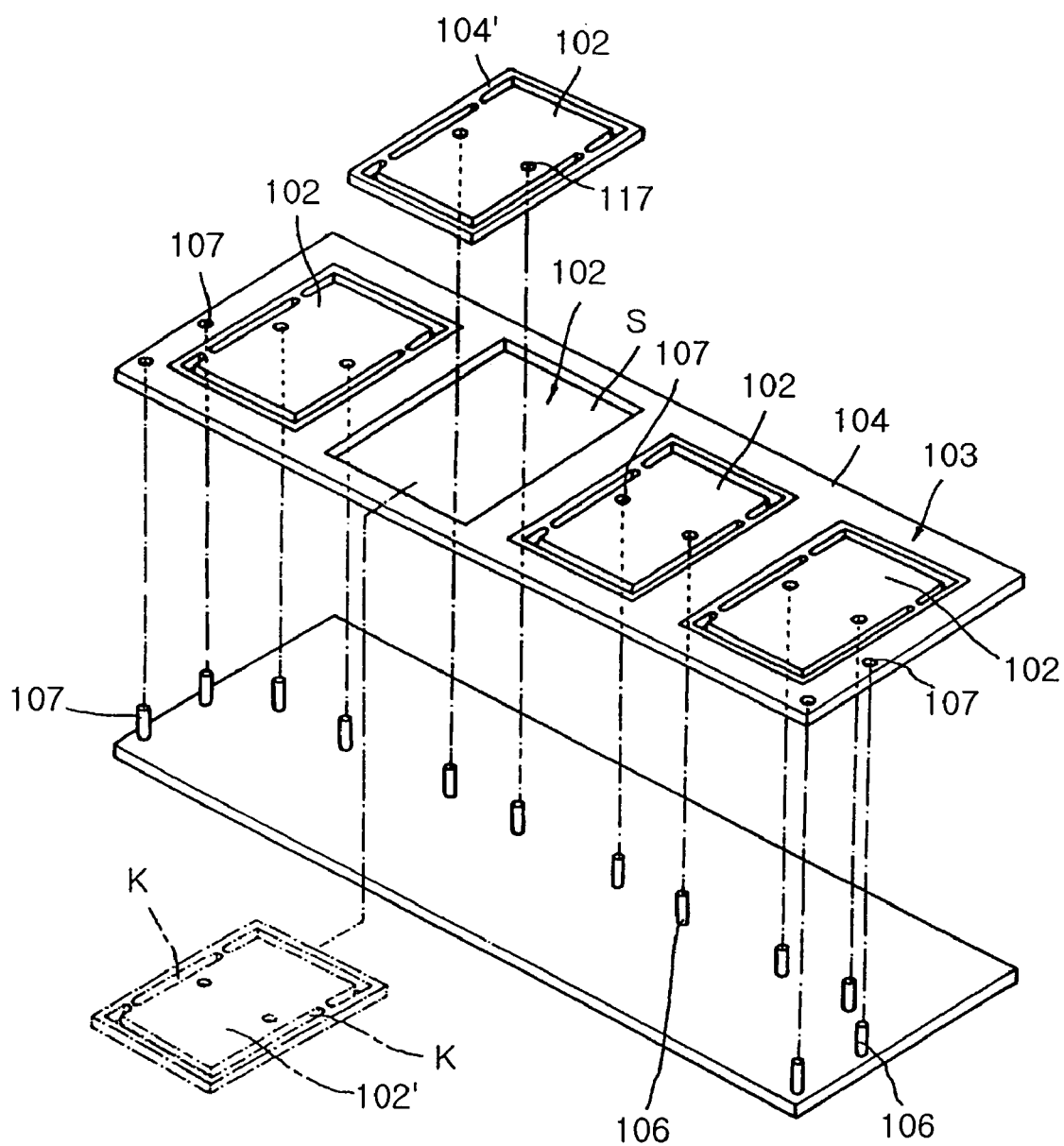
FIG. 7 is a schematic perspective view showing the coupled state of the first and second PCB sheets in the second embodiment of the present invention.
Figure 8:
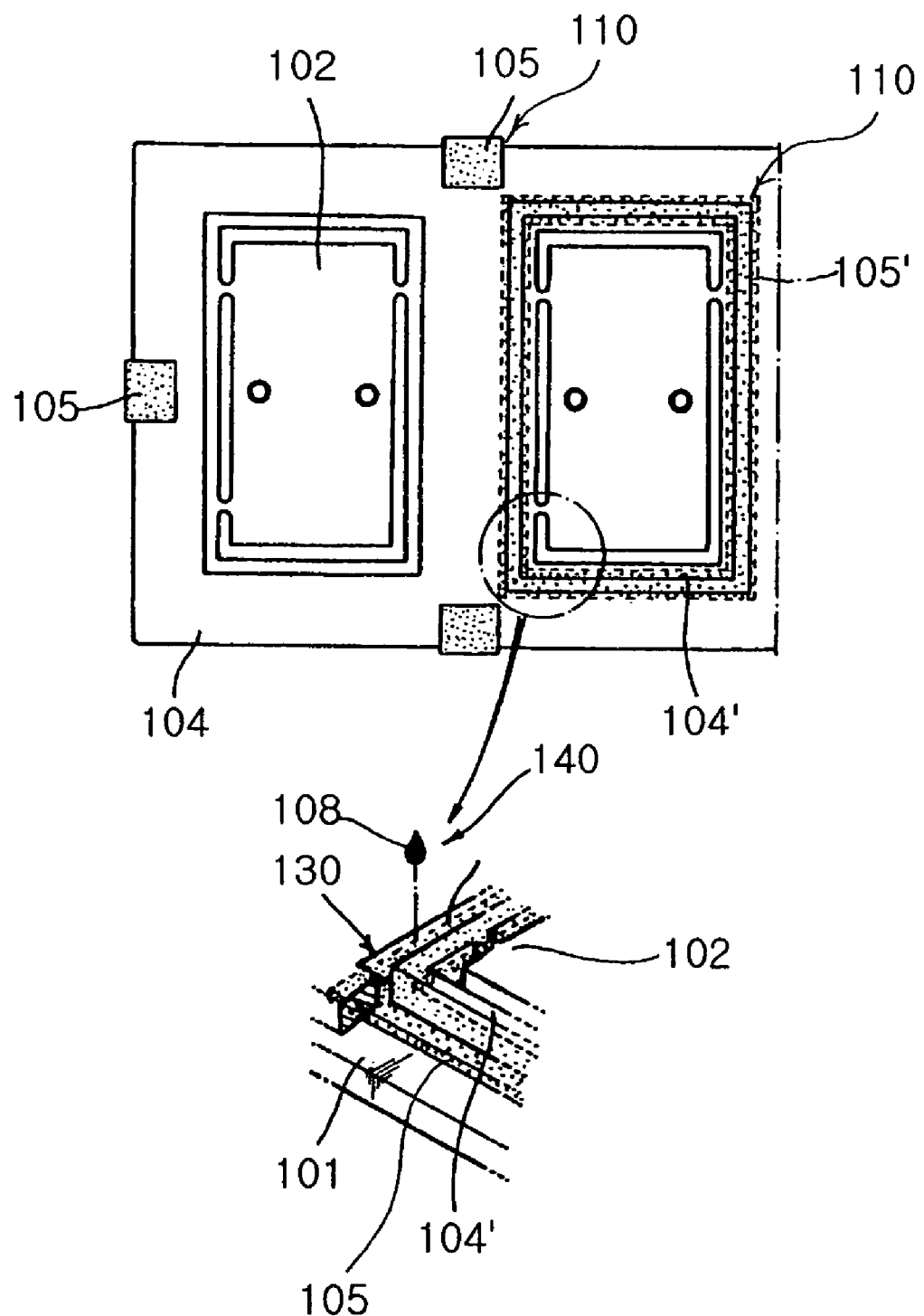
FIG. 8 illustrates in detail the coupling portion of the first and second PCB sheets according to the present invention.

FIGS. 6 and 7 illustrate a state in which the second PCB sheet is inserted into the first PCB sheet, and the two sheets are fixed onto the PCB securing plate, in a second embodiment of the present invention. FIG. 8 illustrates in detail the coupling portion of the first and second PCB sheets according to the present invention.

If any one of continuously printed circuit pattern parts 102 (printed on a first PCB sheet 104) is found to be a defective circuit pattern part 102', then the rectangular portion of the defective circuit pattern part 102' which is defined by a separation groove K is cut off by using a router or the like to form a blanked space S. Then a second PCB sheet 104' with a new good-quality circuit pattern 102 printed thereon is placed into the rectangular space S, and then, the first and second PCB sheets 104 and 104' are located by using a PCB securing means 110.

The first and second PCB sheets 104 and 104' are installed on the PCB securing plate 101 by using a PCB securing tape 105 which is one of the elements of the PCB securing means 110.

A plurality of PCB securing pins 106 upstand upon the PCB securing plate 101, while the first and second PCB sheets 104 and 104' are provided with a plurality of pin receiving holes 107 correspondingly with the PCB securing pins 106. The PCB securing pins 106 and the pin receiving holes 107 constitute a PCB position locating means 120. Thus the PCB securing pins 106 of the PCB securing plate 101 are inserted into the pin receiving holes 107 to support the PCB sheets 104 and 104'.

Figure 9:
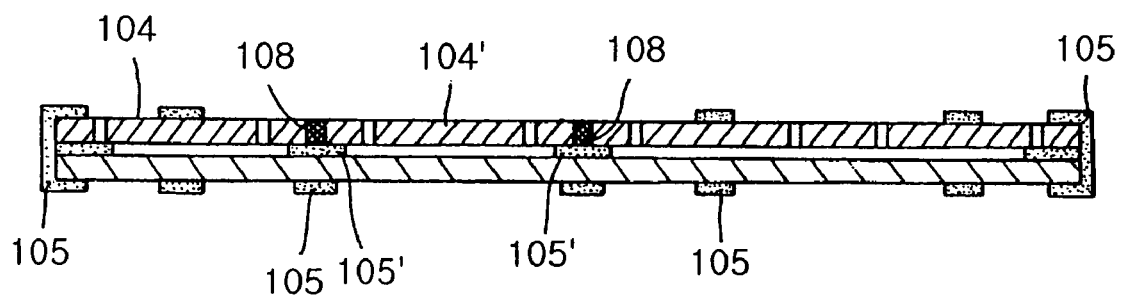
FIG. 9 is a frontal sectional view showing the coupled state of the first and second PCB sheets of FIG. 8.

Further as shown in FIG. 9, between the first and second PCB sheets 104 and 104', there is formed a space 130 to form a channel 109, so that an adhesive 108 as an adhesive means 140 can be injected into the channel 109. On the bottom of the channel 109, there is put a PCB securing tape 105' to prevent any leakage of the adhesive 108.

A cover part 10 is put on the first and second PCB sheets 104 and 104' which are secured on the PCB securing plate 101 like in the first embodiment. Thus the circuit pattern part 102 of the first and second PCB sheets 104 and 104' are protected from the heat. The adhesive 108 is injected into the channel 109, and the injected adhesive 108 is exposed to the outside so as to be cured. In this manner, the first and second PCB sheets 104 and 104' are coupled together.

Accordingly, as shown in FIGS. 6 to 9, if any one of the circuit pattern parts 102 of the PCB sheet 103 is found be a defective circuit pattern part 102', then the defective circuit pattern part 102' is cut away along the groove K to form a blanked space S like in the first embodiment. Then a second PCB sheet 104' on which a good quality circuit pattern part 102 is printed is placed into the blanked space S, and then, the second PCB sheet 104' is coupled to the first PCB sheet 104.

Under this condition, the reason why the blanked space S is formed in a rectangular shape is as follows. That is, when the finished PCB product is carried to a subsequent process to install chip components and other electronic components, the weakness of the coupling portion between the first and second PCB sheets 104 and 104' is reinforced by providing a rectangular blanked space, because the rectangular space increases the coupling area.

After completion of the blanking of the PCB sheet portion of the defective circuit pattern part 102', a second PCB sheet 104' on which a good quality circuit pattern is printed is placed into the blanked space S of the first PCB sheet 104. The whole structure including the first and second PCB sheets 104 and 104' is disposed on the PCB securing plate 101 to be secured on it. Under this condition, the PCB securing pins 106 of the PCB securing plate 101 are inserted into the pin receiving holes 107 to support the PCB sheets 104 and 104', so that the first and second PCB sheets 104 and 104' would be secured on the PCB securing plate 101.

In order to prevent any loose movements of the first and second PCB sheets 104 and 104', a PCB securing tape 105 which is a both-face tape is put to around the coupling portion between the first and second PCB sheets 104 and 104' and on the bottom of the PCB sheet so as to be attached on the PCB securing plate 101.

Further, between the first and second PCB sheets 104 and 104' which are disposed on the PCB securing plate 101, there is provided a separation distance of about 1–5 mm. Thus there is formed a space 130 which forms a channel 109. Then a heat resistant tape 105' is put to the bottom, front and rear of the channel 109, so that the injected adhesive can be prevented from being leaked.

Thus the first and second PCB sheets 104 and 104' are secured by using the PCB securing tape 105 and the tape 105', the latter surrounding the channel 9 of the space 13. Then the adhesive 108 is injected into the channel 109 of the space 130 which is formed between the first and second PCB sheets 104 and 104'. Then the whole structure is transferred to a drying furnace to make the adhesive 108 cured. Further, a hardening agent such as a highly heat resistant epoxy resin is added to the adhesive. After the injection of the adhesive 108, the circuit patterns of the first and second PCB sheets 104 and 104' are covered with a flat cover part 10 to protect the first and second PCB sheets 104 and 104' from the heat like in the first embodiment.

Then the tape 105 which has been put to around the PCB sheet 104' is removed, and the tape 105' which has been put on the bottom of the channel 109 is also removed. Then, the PCB securing plate 101 is separated from the first and second PCB sheets 104 and 104', thereby completing the coupling of the first and second PCB sheets 104 and 104'.

Figure 10:
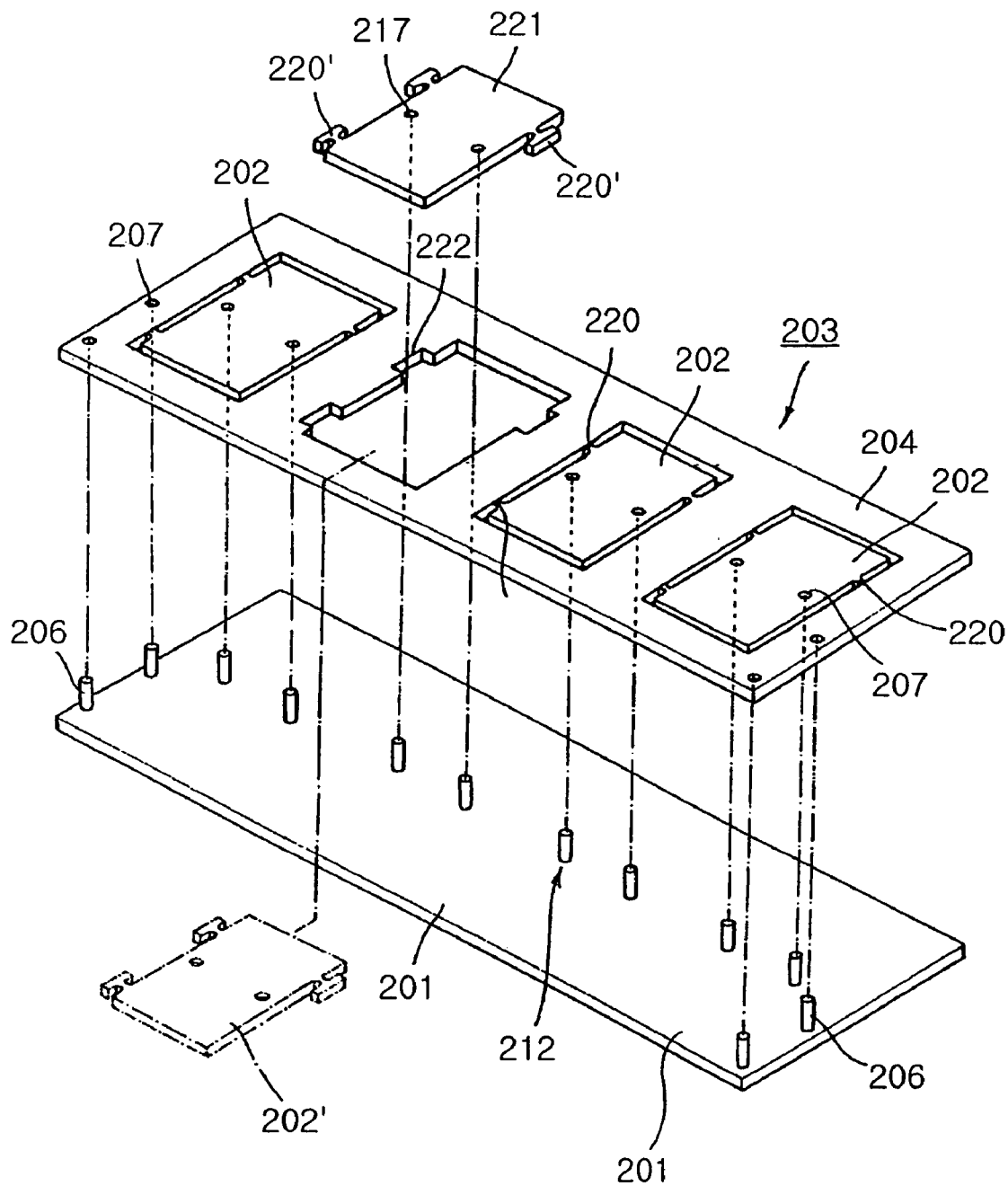
FIG. 10 illustrates a state in which a good quality PCB sheet is inserted into the whole PCB sheet, and the two sheets are fixed onto the PCB securing plate, in a third embodiment of the present invention.
Figure 11:
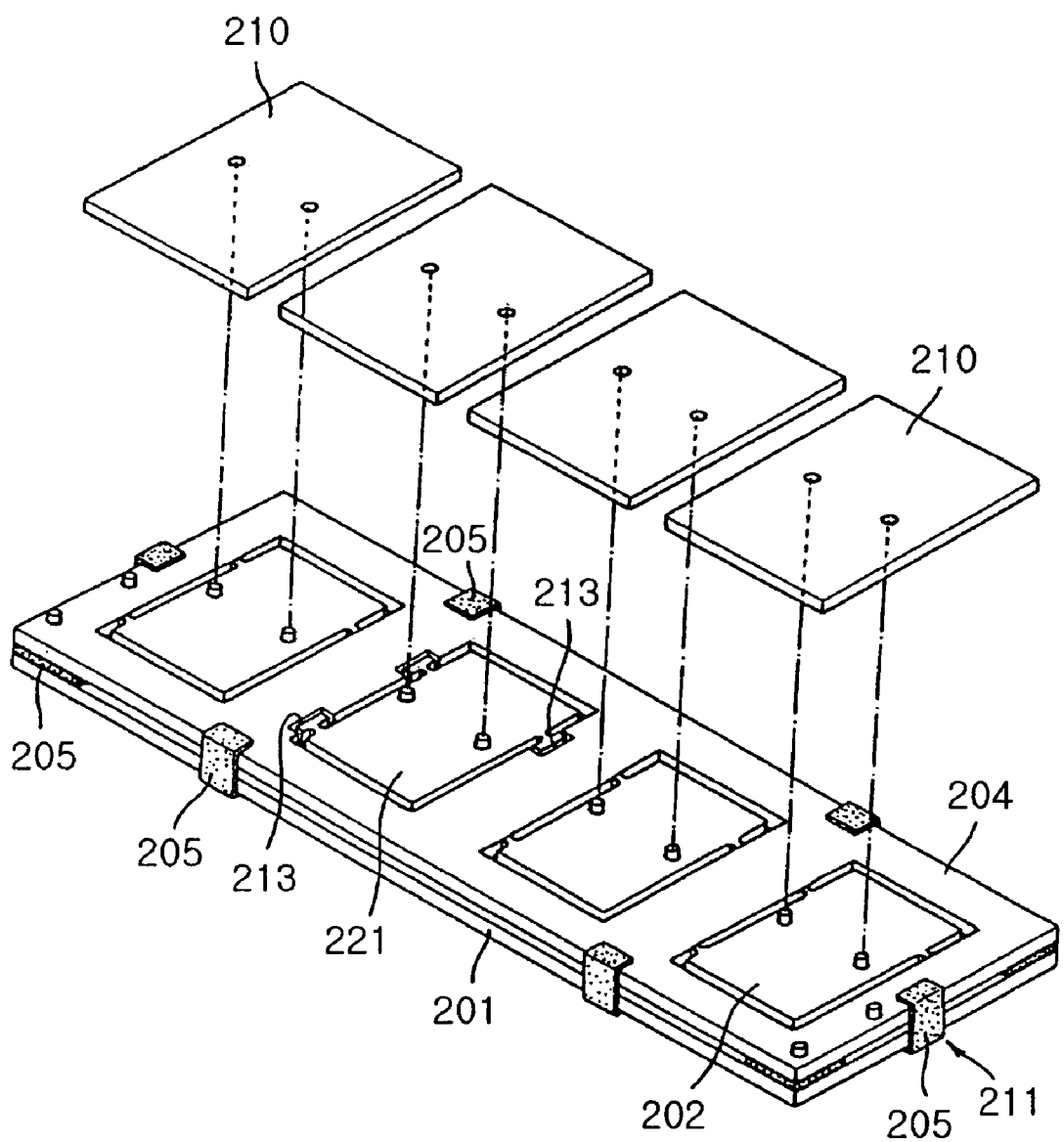
FIG. 11 illustrates a state in which a good quality PCB sheet is coupled into a space formed by the removal of the defective PCB sheet in the third embodiment of the present invention.

FIG. 10 illustrates a state in which a good quality PCB sheet is inserted into the whole PCB sheet, and the two sheets are fixed onto the PCB securing plate, in a third embodiment of the present invention. FIG. 11 illustrates a state in which a good quality PCB sheet is coupled into a space formed by the removal of the defective PCB sheet in the third embodiment of the present invention.

A PCB sheet 204 on which a plurality of PCBs 202 are connectedly installed through a plurality of connecting parts 220 is disposed a PCB securing plate 201. If a defective PCB 202' is found among the plurality of the PCBs 202, then the defective PCB 202' is cut out along a PCB separating groove K. Then a good quality PCB 221 with connecting parts 220' is fitted into the cut-out space 222 to be secured to the PCB sheet.

Figure 12B:
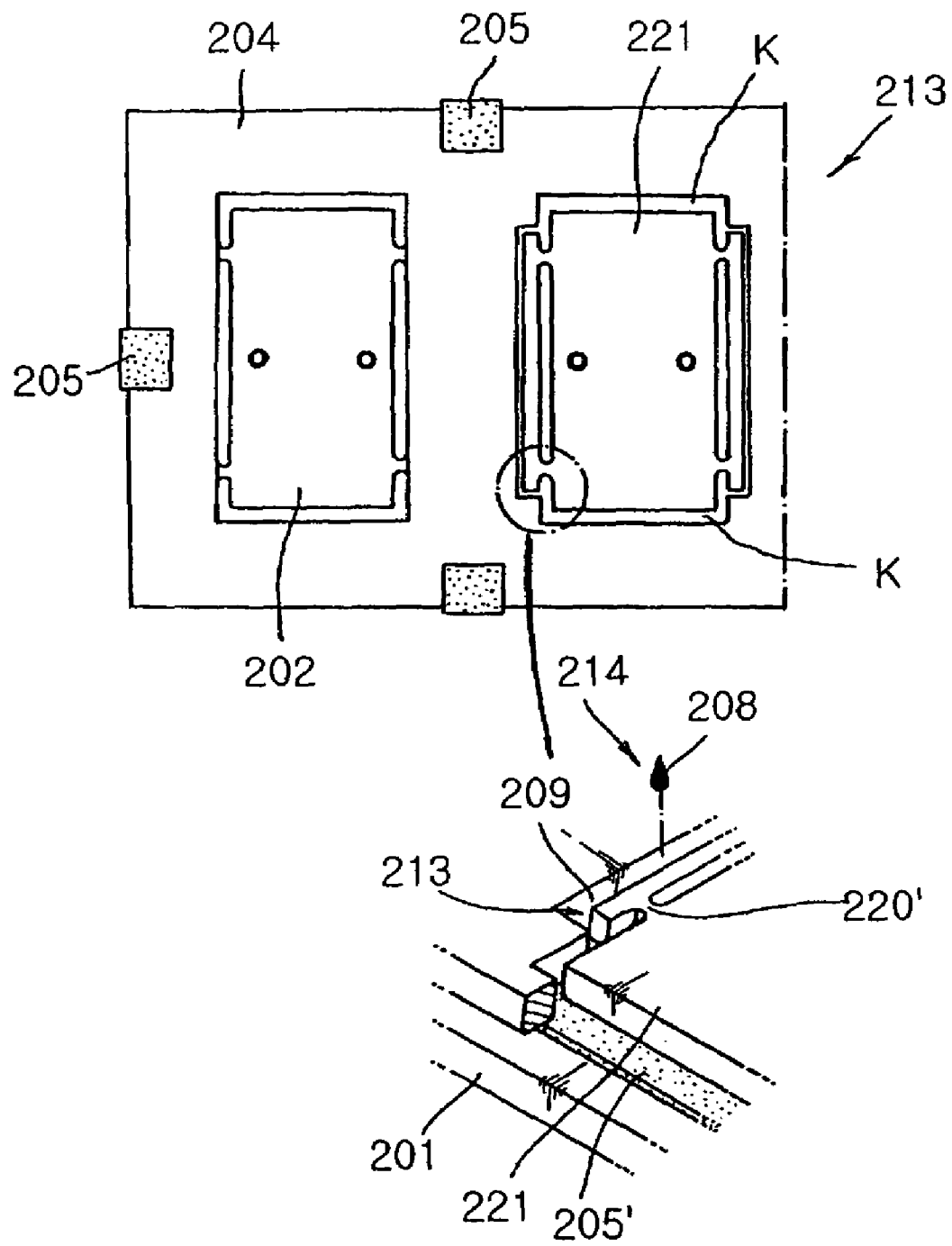

As shown in FIGS. 12A and 12B, the removal of the defective PCB 202' is carried out in the following manner. That is, either a cutting is carried out around the connecting parts 220 (as shown in FIG. 2A), or the plurality of the connecting parts 220 of the PCB 202 are cut off (FIG. 2B). The reason is as follows. That is, when carrying the PCB sheets to a subsequent process, the carrying posture becomes different depending on the circuit pattern arrangement direction on the PCB sheet. Therefore, when installing chip components or other electronic components into the PCB 202 of the PCB sheet 204, the joining portion of the good quality PCB 221 has to be made to have a high strength. For this purpose, the joining portion is selectively made long or short.

Figure 13:
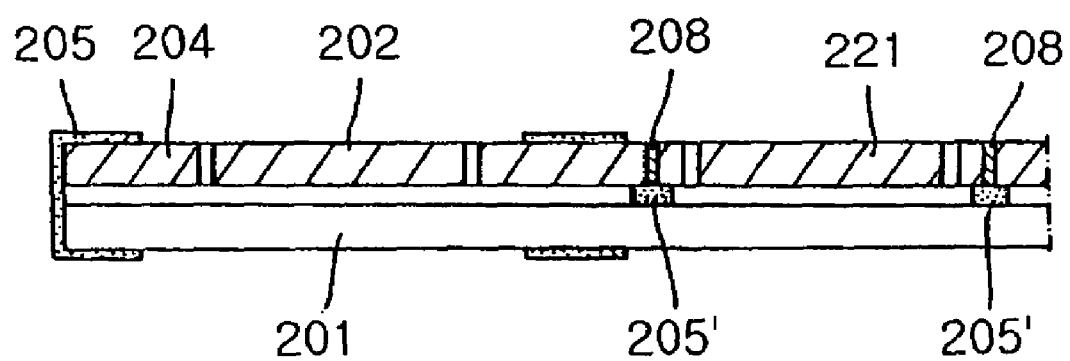
FIG. 13 is a frontal sectional view showing the whole PCB sheet and a new good quality PCB sheet.

As shown in FIG. 13, a PCB securing tape 205 which is a both-face tape is put around and on the bottom of the coupling portion of the good quality PCB 221 to prevent any loose movements of the PCB sheet 204 and the good quality PCB 221. In this manner, the PCB sheet 204 and the good quality PCB 221 are fixed to the PCB securing plate 201.

A plurality of PCB securing pins 206 upstand upon the PCB securing plate 201, while the PCB sheet 204 and the good quality PCB 221 are provided with a plurality of pin receiving holes 207 correspondingly with the PCB securing pins 206. These pins and holes are for locating each of the PCB sheets 204 at exact position and are for carrying the PCB sheets 204.

Between the PCB sheet 204 and the good quality PCB 221, there is formed a space 213 to form a channel 209, so that an adhesive 208 as an adhesive means 214 can be injected into the channel 209. On the bottom, front and rear of the channel 209, there is put a PCB securing tape 205' to prevent any leakage of the adhesive 208.

Further, a cover 210 is covered on the good quality PCB 221 and the PCB 202 of the PCB sheet 204 which is secured on the PCB securing plate 201. Thus the PCBs 202 of the PCB sheet 204 are protected from the ambient heat, and the adhesive 208 is injected into the channel 209 to be cured, thereby coupling a second PCB sheet 204' (with the good quality PCB 221 printed thereon) to the first PCB sheet 204.

Figure 14:
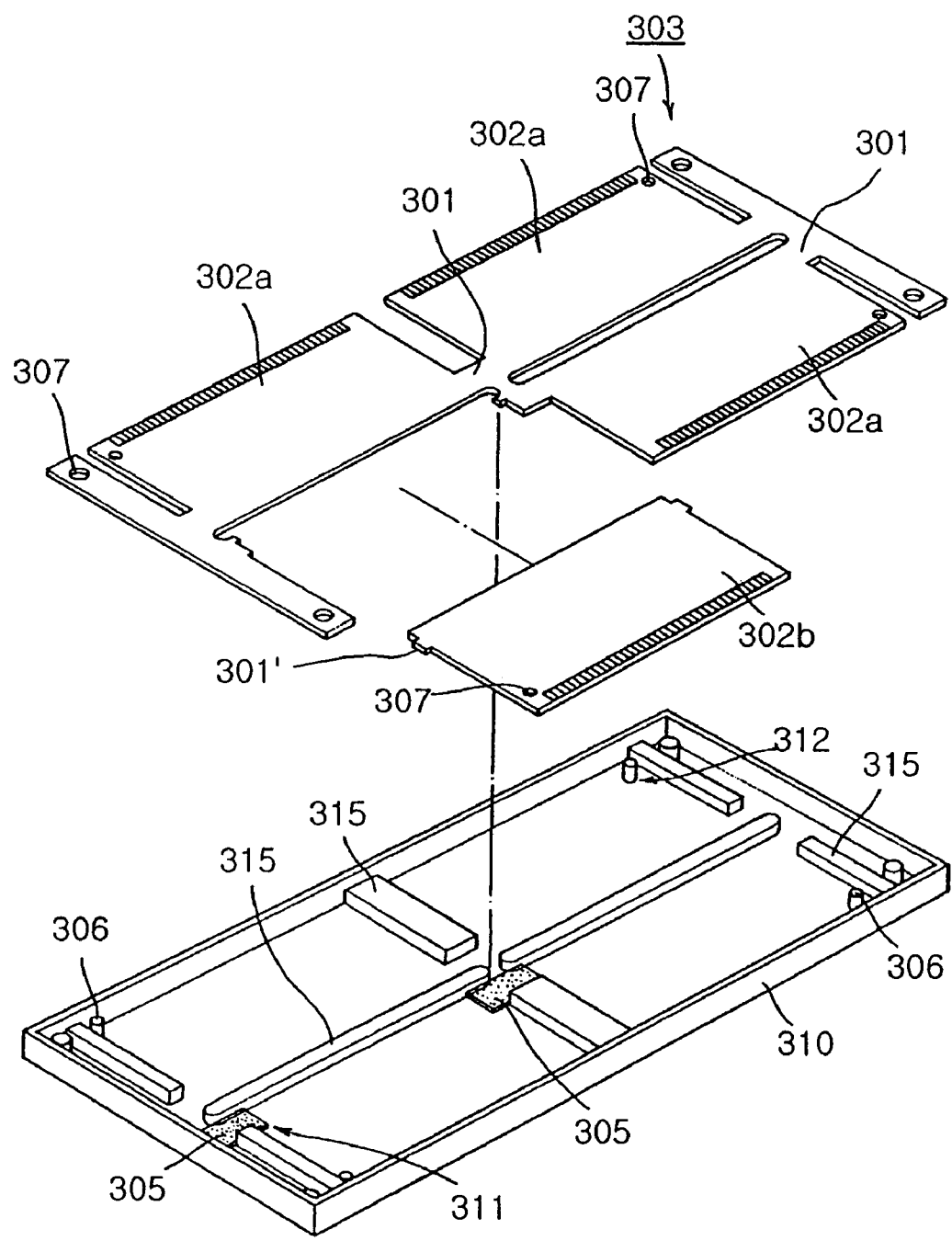
FIG. 14 illustrates a state in which a good quality PCB sheet is inserted into the whole PCB sheet, and the two sheets are fixed onto the PCB securing plate by using a securing jig, in a fourth embodiment of the present invention.
Figure 15:
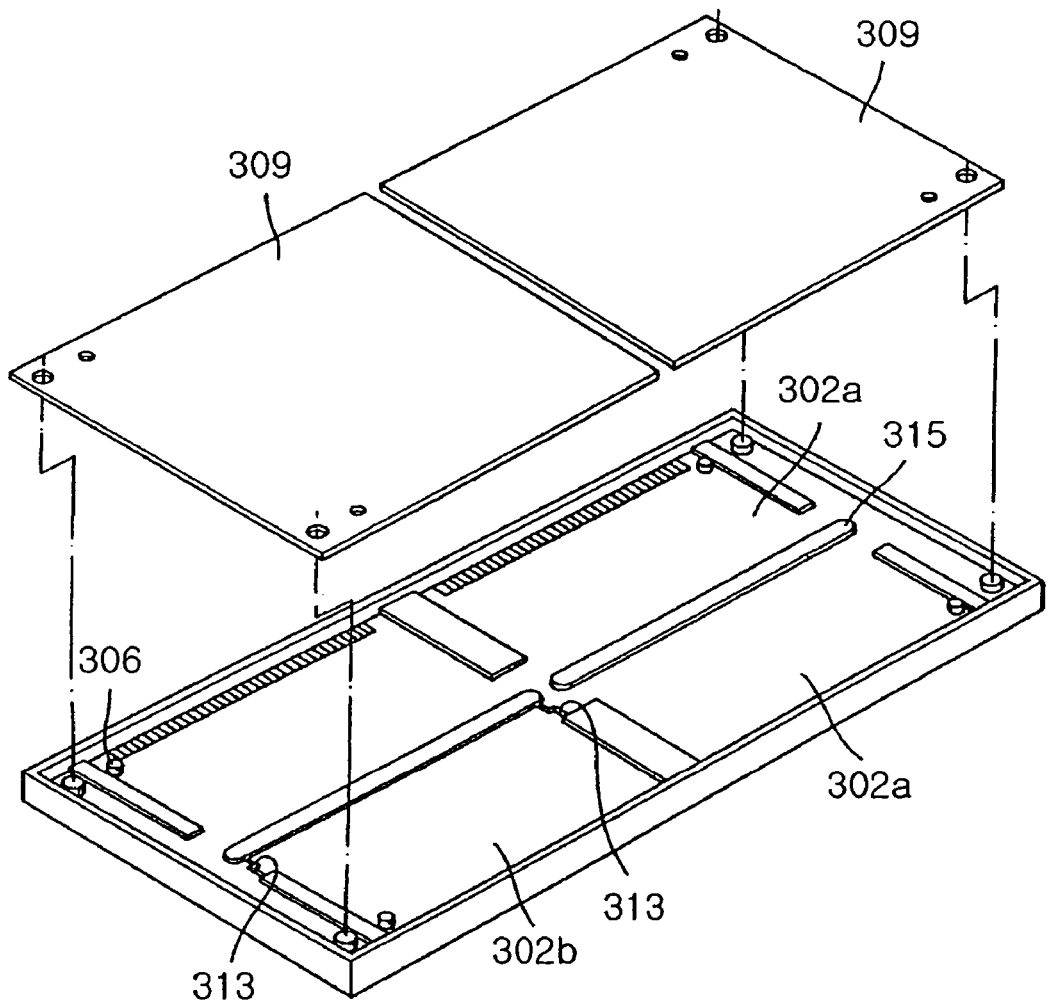
FIG. 15 is a schematic perspective view showing the coupling of a new good quality PCB sheet to the whole PCB sheet in the fourth embodiment of the present invention.
Figure 16:
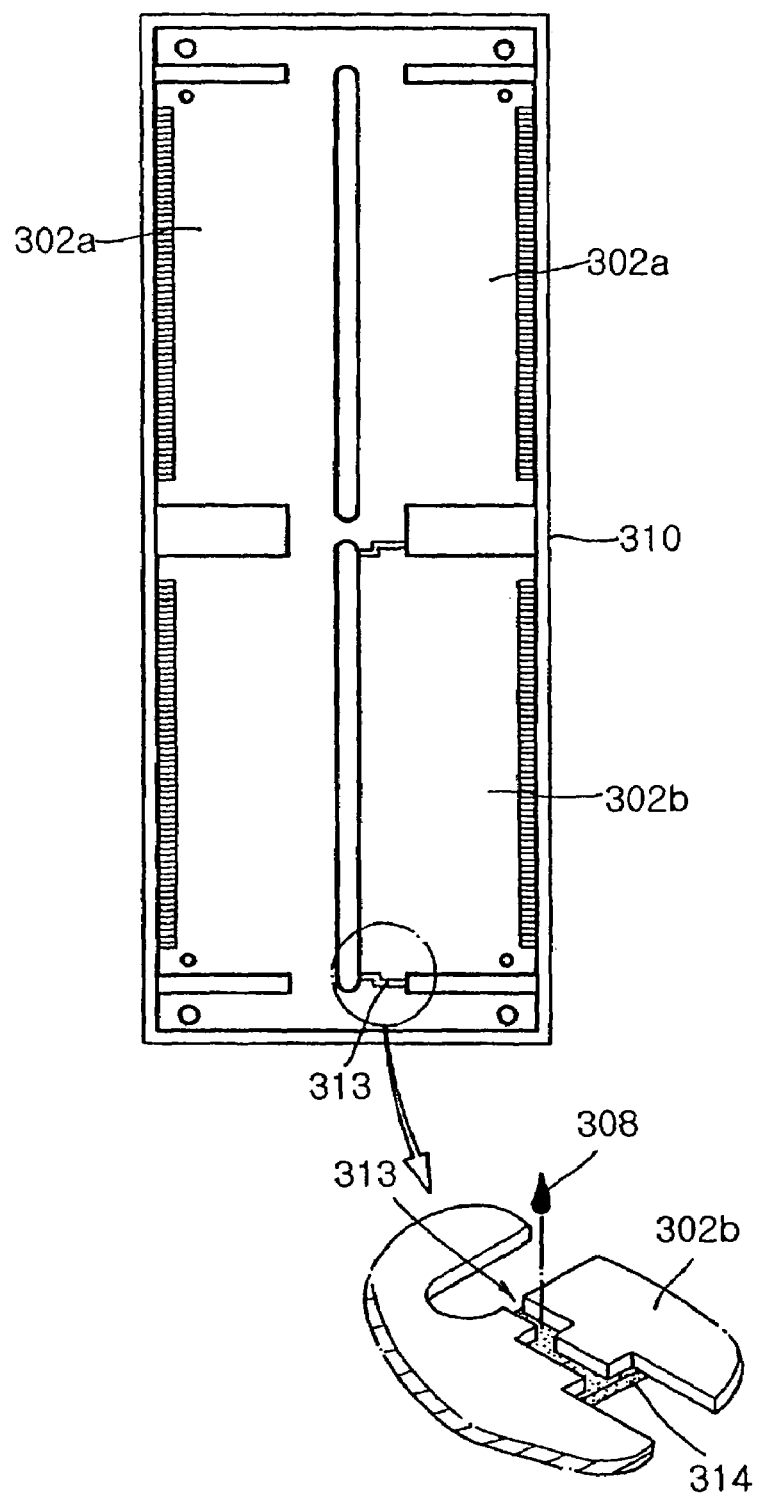
FIG. 16 is a plan view showing the coupling of a new good quality PCB sheet to the whole PCB sheet of FIG. 15.

FIGS. 14 and 15 illustrate a state in which a good quality PCB sheet is inserted into the whole PCB sheet, and the two sheets are fixed onto the PCB securing plate by using a securing jig, in a fourth embodiment of the present invention. FIG. 16 is a plan view showing the coupling of a new good quality PCB sheet to the whole PCB sheet of FIG. 15.

A PCB 303 consists of a plurality of circuit pattern parts 302a which are connected to each other by connecting parts 301. If a defective circuit pattern part is found among the plurality of the circuit pattern parts 302a upon carrying out a testing, then the defective circuit pattern part is removed by cutting a connecting part 301'. In the place of the removed defective circuit pattern part, there is placed a good quality circuit pattern part 302b by means of a PCB securing means 311 into a PCB securing jig 310 which has a plurality of separating walls 315.

As shown in FIG. 16, the good quality circuit pattern part 302b has to be secured in the place of the removed defective circuit pattern part. For this purpose, a PCB securing tape 305 which is a both-face tape is put on the bottom of the coupling portion, so that any loose movements of the good quality circuit pattern part 302b can be prevented, thereby securing it to the PCB securing jig 310.

A plurality of PCB securing pins 306 upstand upon the PCB securing jig 310, while the PCB 303 and the good quality circuit pattern part 302b are provided with a plurality of pin receiving holes 307. The plurality of the PCB securing pins 306 and the plurality of the pin receiving holes 307 constitute a PCB position locating means 312. Thus the PCB securing pins 306 of the PCB securing jig 310 are inserted into the pin receiving holes 307 of the PCB 303 and the good quality circuit pattern part 302b. Thus the good quality circuit pattern part 302b is secured at a side of the PCB 303 within the PCB securing jig 310.

Between the PCB 303 and the good quality circuit pattern part 302b, there is formed a space 313 which forms a channel. An adhesive 308 which is an adhesive means 314 is injected to the channel.

Figure 17:
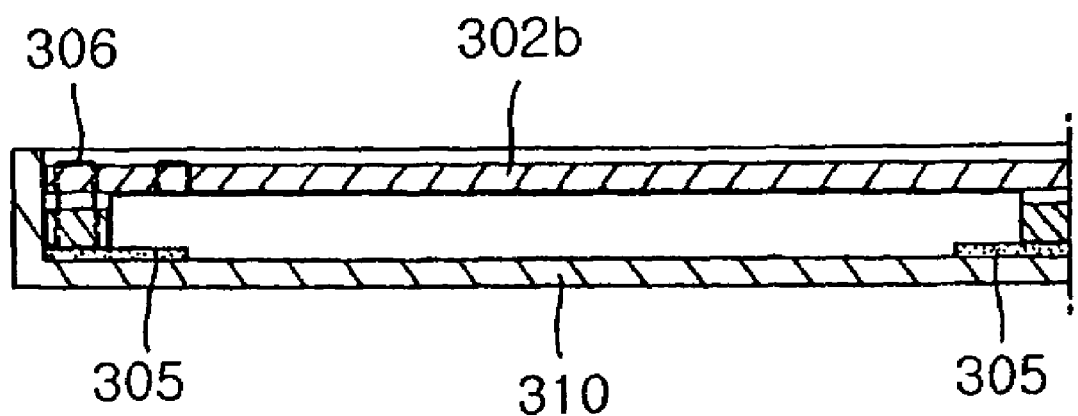
FIG. 17 is a frontal sectional view showing the whole PCB sheet and a new good quality PCB sheet of FIG. 15.

As shown in FIG. 17, a cover 309 covers the good quality circuit pattern part 302b and the PCB 303 on which a plurality of circuit patterns 302a are formed. In this manner, the good quality circuit pattern part 302b and the PCB 303 are protected from the ambient heat. Meanwhile, the adhesive 308 which has been injected into the channel of the space 313 is cured by being exposed to the external air, so that the good quality circuit pattern part 302b can be firmly coupled to the PCB 303.

According to the present invention as described above, if a defective circuit pattern is found among the plurality of the circuit patterns, then the defective circuit pattern is removed to replace it with a good quality circuit pattern so as to secure it in place in an easy manner. By removing the defective circuit pattern, the whole PCB sheet which is otherwise to be discarded can be saved, thereby increasing the product yield and curtailing the production cost. That is, the PCB sheet on which a defective circuit pattern is printed is cut off, and the cut space is filled with a good quality circuit pattern sheet by means of a position locating means. Then a heat resistant tape and an adhesive means are used to secure the good quality circuit pattern sheet to the whole PCB sheet in an easy manner. Accordingly, in manufacturing the printed circuit board of the present invention, the workability and the productivity are drastically improved.

In the above, the present invention was described based on the specific embodiments and the attached drawings, but it should be apparent to those ordinarily skilled in the art that various changes and modification can be added without departing from the spirit and scope of the present invention which will be defined by the appended claims.

What is claimed is:

1. A device for coupling a PCB sheet, comprising:
   a position deciding jig part for receiving a PCB sheet with a plurality of circuit patterns printed thereon and a replaced good quality circuit pattern sheet, after a defective circuit pattern sheet is cut away, and after said good quality circuit pattern sheet is placed into a space of said removed defective circuit pattern sheet;
   a PCB securing means attached on said PCB securing plate, for preventing any loose movements of said PCB sheet and said good quality circuit pattern sheet, both of them inserted into said jig part; and
   an adhesive means filled into a space between said PCB sheet and said replaced good quality circuit pattern sheet to be cured so as to couple them together.

2. The device as claimed in claim 1, further comprising a position locating means said position locating means consisting of a plurality of PCB securing pins upstanding on said PCB securing jig part, and a plurality of pin receiving holes formed in said PCB sheet and on said good quality circuit pattern sheet, said PCB securing pins being inserted into said pin receiving holes.

3. The device as claimed in claim 1, wherein said PCB securing jig part comprises a plurality of separating walls to separate said sheets of said PCB sheet and said good quality circuit pattern sheet from each other.

4. The device as claimed in claim 1, wherein said PCB securing means is a heat resistant tape for preventing thermal deformations.

5. The device as claimed in claim 4, wherein said heat resistant tape is a both face tape to secure said PCB and said good quality circuit pattern sheet to said jig.

6. The device as claimed in claim 1, wherein said space for coupling said PCB sheet and said good quality circuit pattern sheet together forms a channel.

7. The device as claimed in claim 1, wherein said adhesive means a high temperature adhesive for preventing thermal deformations.

8. The device as claimed in claim 1, further comprising a flat cover disposed on said circuit patterns of said PCB sheet or said good quality circuit pattern sheet to protect the same.

9. The device as claimed in claim 1, wherein said space formed between said PCB sheet and said good quality circuit pattern sheet for receiving said adhesive means has a width of 1 to 5 mm between said PCB sheet and said good quality circuit pattern sheet.

10. A device for coupling a PCB sheet, comprising:
a position deciding jig part for receiving a PCB sheet with a plurality of circuit patterns printed thereon and a replaced good quality circuit pattern sheet, after a defective circuit pattern sheet is cut away, and after said good quality circuit pattern sheet is placed into a space of said removed defective circuit pattern sheet;
a PCB securing element attached on said PCB securing plate, for preventing any loose movements of said PCB sheet and said good quality circuit pattern sheet, both of them inserted into said jig part; and
an adhesive element filled into a space between said PCB sheet and said replaced good quality circuit pattern sheet to be cured so as to couple them together.

11. The device as claimed in claim 10, further comprising a position locating element said position locating element consisting of a plurality of PCB securing pins upstanding on said PCB securing jig part, and a plurality of pin receiving holes formed in said PCB sheet and on said good quality circuit pattern sheet, said PCB securing pins being inserted into said pin receiving holes.

12. The device as claimed in claim 10, wherein said PCB securing jig part comprises a plurality of separating walls to separate said sheets of said PCB sheet and said good quality circuit pattern sheet from each other.

13. The device as claimed in claim 10, wherein said PCB securing element is a heat resistant tape for preventing thermal deformations.

14. The device as claimed in claim 13, wherein said heat resistant tape is a both face tape to secure said PCB and said good quality circuit pattern sheet to said jig.

15. The device as claimed in claim 10, wherein said space for coupling said PCB sheet and said good quality circuit pattern sheet together forms a channel.

16. The device as claimed in claim 10, wherein said adhesive element a high temperature adhesive for preventing thermal deformations.

17. The device as claimed in claim 10, further comprising a flat cover disposed on said circuit patterns of said PCB sheet or said good quality circuit pattern sheet to protect the same.

18. The device as claimed in claim 10, wherein said space formed between said PCB sheet and said good quality circuit pattern sheet for receiving said adhesive element has a width of 1 to 5 mm between said PCB sheet and said good quality circuit pattern sheet.

* * * * *